US00PP21379P2

(12) United States Plant Patent
Scorza

(10) Patent No.: US PP21,379 P2
(45) Date of Patent: Oct. 12, 2010

(54) PEACH TREE NAMED 'KV981175'
(50) Latin Name: ***Prunus persica* (L.) Batsch**
Varietal Denomination: KV981175

(75) Inventor: Ralph Scorza, Shepherdstown, WV (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/316,077

(22) Filed: Dec. 9, 2008

(51) Int. Cl.
*A01H 5/00* (2006.01)

(52) U.S. Cl. ..... Plt./198
(58) Field of Classification Search ..... Plt./198
See application file for complete search history.

*Primary Examiner*—Annette H Para
(74) *Attorney, Agent, or Firm*—John D. Fado; Evelyn M. Rabin

(57) ABSTRACT

A new and distinct variety of peach tree which is characterized by an upright tree growth form; producing yellow, melting-flesh fruit of excellent dessert-quality flavor, of large size with approximately 80% red blush over a yellow ground color, ripening in late mid-season.

3 Drawing Sheets

BACKGROUND OF THE NEW VARIETY

The present invention relates to a new and distinct variety of peach tree [*Prunus persica* (L.) Batsch] which is named 'KV981175'.

The new variety was originated at the Appalachian Fruit Research Station, Agricultural Research Service, U.S. Department of Agriculture in Kearneysville, W. Va. and was identified as KV981175. The present new variety, selected as KV981175, resulted from hand pollination of 'Bounty' peach with pollen of 'Crimson Rocket' (U.S. Plant Pat. 15,216 P2). The parentage of 'Bounty' is [(Halberta open pollinated)×Redskin]×[Loring×[(Hiley×Fireglow)×Fireglow]]. The parentage of 'Crimson Rocket' is (Flavortop nectarine×"pillar")×[(Suncrest×K2)×"pillar"].

It was selected in 2001 from a group of 137 seedlings of the before said hybridization. It was vegetatively propagated by bud-grafting on to standard rootstock. The tree was propagated by a commercial nursery in Pennsylvania. Propagated trees were grown at the USDA-ARS-Appalachian Fruit Research Station and evaluated for trueness to type at that location in proximity to the original tree that was the source of propagative material. Testing for 7 years has shown that said variety maintains high fruit quality, productivity, and maintains its upright tree form when bud-grafted onto standard rootstocks. No aberrant types have appeared.

KV981175 is diploid, self-fertile and is cross compatible as a male or female parent with other peach varieties. No pollination incompatibilities have been noted.

This new variety is distinct from it parents in its combination of high fruit quality, late mid-season time of ripening, and upright growth habit.

This variety is distinct from other peach cultivars in its combination of an upright growth habit, which is conditioned by the br gene in a heterozygous state (Brbr) [see Scorza et al., 2002. *J. Amer. Soc. Hort. Sci.* 127 (2) 254-261] and in its production of large size mid-season ripening fruit of excellent desert quality. The growth habit of trees is distinctly upright. The firm melting flesh does not cling to the stone. Fruit are melting flesh, dessert type. Flesh is yellow, flavorful and firm until full-ripe. The fruit outer appearance is characterized by a red blush over 80% of the surface and a yellow ground color. Fruit have yellow ground color with red blush that covers approximately 80% of the fruit surface at maturity. Fruit size average 70-77 mm in diameter with an average weight of 234 g. Fruit are sweet with a good balance of acidity. Brix of firm-ripe fruit averages between 12 and 14° depending on date of harvest and environment. Fruit maintain firmness on the tree and in storage at levels comparable to commercial peach cultivars.

SUMMARY OF THE INVENTION

A peach tree with a distinctly upright growth form, suitable for standard-density and high-density plantings; producing yellow, melting-flesh fruit of excellent dessert-quality flavor, of large size with approximately 80% red blush over a yellow ground color.

BRIEF DESCRIPTION OF THE DRAWINGS

FIG. 1 is a photograph of the fruit of the KV981175 peach in full color showing the ripe fruit viewed in profile and sectioned in half from end to end, with one-half of the fruit shown with the stone in place in the flesh.

FIG. 2 is a full color photograph of the fruit of the KV981175 peach on the tree.

FIG. 3 is a full color photograph of representative stems of flowers of the KV981175 peach at full bloom.

The figures show photographs in color as accurate as reasonably possible to attain in color photographic reproductions of this type.

DETAILED DESCRIPTION OF THE NEW VARIETY

The following is a detailed description of the botanical and pomological characteristics of the subject peach. Color data are presented in Royal Horticultural Society (R.H.S.) Color Chart designations. Where dimensions, sizes, color, and other characteristics are given, it is to be understood that such characteristics are approximations of averages set forth as accurately as practicable.

Age and growing conditions of plant observed and The descriptions reported herein are from specimens grown at Kearneysville, W. Va. Data was taken from a 10 year old tree growing on its own roots growing at the USDA-ARS Appalachian Fruit Research Station—GPS coordinates 39° 21' 18" N, 77° 52' 41" W. The tree was planted in a field that received 40 lbs of nitrogen per acre. Field evaluations under a normal program of disease and pest control (see 2010 Spray Bulletin for Commercial Tree Fruit Growers, D. G. Pfeiffer et al. Virginia Cooperative Extension Publication 456-419 [Retrieved from the Internet: www.ext.vt.edu]) show no marked susceptibility to pathogens or insects when compared with peach varieties adapted to the eastern U.S. such as 'Bounty', 'Sweet-N-Up', and 'Sentry'. Measurements below are for the tree of the size and location as indicated above.

Tree:

*Size.*—Tree height: 3.2 m; tree width: 4.06×4.96 m.
*Vigor.*—Vigorous.
*Growth.*—Upright.
*Density.*—Medium dense to dense.
*Productivity.*—Productive.
*Bearing.*—Regular.

Trunk:

*Size.*—Trunk diameter 10 cm above ground: 19.3 cm.
*Color.*—Brown RHS N 200 D over greyed-red 180 A on sun-exposed areas, greyed-red 178 C on shade-exposed areas.
*Bark.*—Lenticel color: greyed orange N170C, edges brown group N200C. Lenticel size: 6.2 mm×1.87 mm.

Branches:

*Size.*—Average scaffold diameter at the point of attachment to trunk: 4.6 cm; average scaffold length: 194 cm.
*Texture.*—Smooth to medium rough, varies with maturity.
*Color.*—Brown RHS N200 D over greyed-red 180 A on sun-exposed areas, greyed-red 178 C on shade-exposed areas. Branch angles off supporting limbs range from 41° to 67° with an average of 59°.

Leaves:

*Size.*—Medium; average length 16 cm, average width 3.9 cm.
*Texture.*—Smooth.
*Thickness.*—Medium.
*Margin.*—Crenate.
*Form.*—Lanceolate, with an acuminate apex and an attenuate base.
*Petiole.*—Medium length, medium thickness.
*Glands.*—Reniform; 2-5 per leaf; average 1.4×0.95 mm RHS 154 B to RHS 153 D.
*Color.*—Upper surface — green RHS 137 B; lower surface — green RHS 138 B.

Flowers:

*Petal size.*—Length — 14 mm. Width at widest point — 10 mm. Width at base — 0.85 mm.
*Bloom period.*—Variable depending on weather, late March to mid-April in Eastern Panhandle of West Virginia.
*Color.*—In full bloom white RHS 155 B becoming red-purple RHS 59 C at petal fall.
*Pollen.*—Present.
*Anther number.*—41.
*Sepal color.*—Abaxial — greyed purple 183C; adaxial —yellow-green N144D, veins streaked with greyed-purple 183C.
*Sepals.*—Abaxial pubescent, adaxial glaborous.

Fruit:

*Maturity when described.*—Shipping ripe to eating ripe.
*Average date of harvest.*—Mid August in Kearneysville, W. Va.
*Size.*—Large; diameter axially 73-84 millimeters longitudinal diameter 73-81 mm depending on crop load and environment.

Flesh:

*Ripens.*—Evenly.
*Texture.*—Firm.
*Fibers.*—Small, few, tender.
*Juice.*—Moderate.
*Aroma.*—Moderate.
*Flavor*—Very good.
*Eating quality.*—Very good; average brix of 12 to 14° depending upon date of harvest and environmental conditions.
*Color.*—Yellow-orange RHS 1 B; pit cavity yellow with small amount of red (RHS 53 C) around stone.

Skin:

*Thickness.*—Medium.
*Tendency to crack.*—None.
*Down.*—Moderate; short in length.
*Color.*—Ground color yellow RHS 6 D to 7C with 80% or more of the surface red-purple RHS 59 A with some areas RHS 183 C, over-color red 47 B.
*Use.*—Dessert.
*Market.*—Local and long distance.

Stone:

*Type.*—Freestone.
*Size.*—Medium; average length 41 millimeters, average width 26 mm, average thickness 17 mm.
*Form.*—Obovate.
*Tendency to split.*—None.
*Color.*—Greyed-orange RHS 177 A with areas of RHS greyed-purple 187 B.

I claim:

1. A new and distinct variety of peach tree producing fruit substantially as illustrated and described.

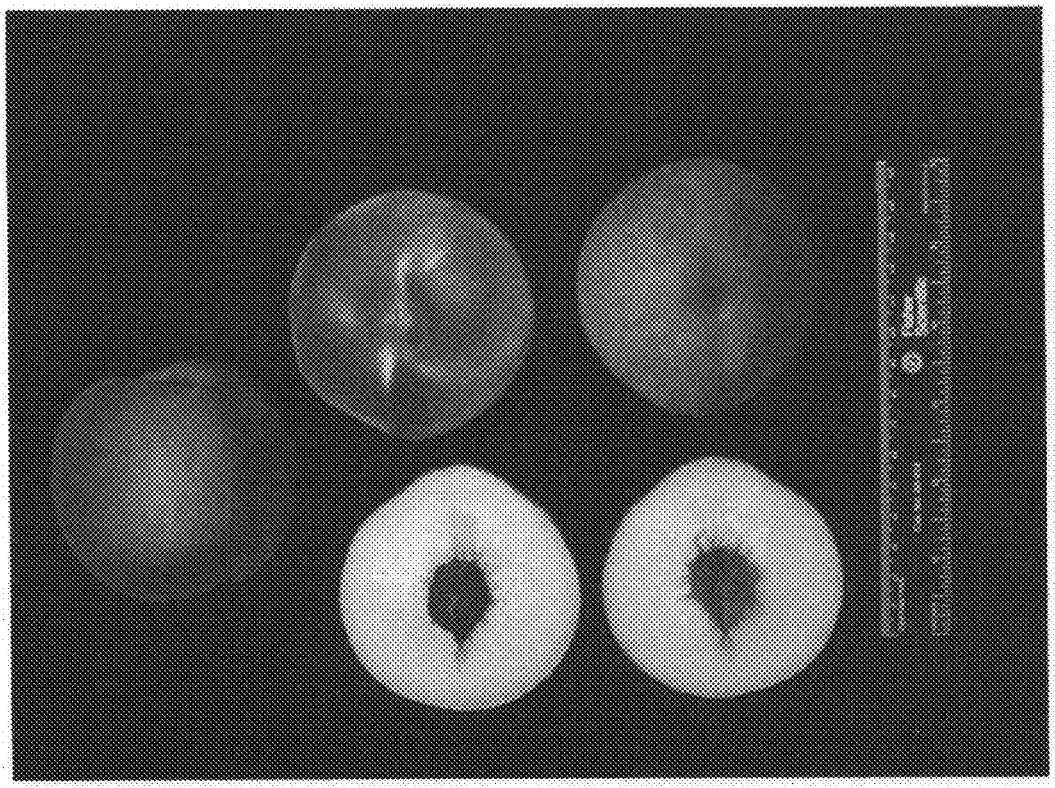

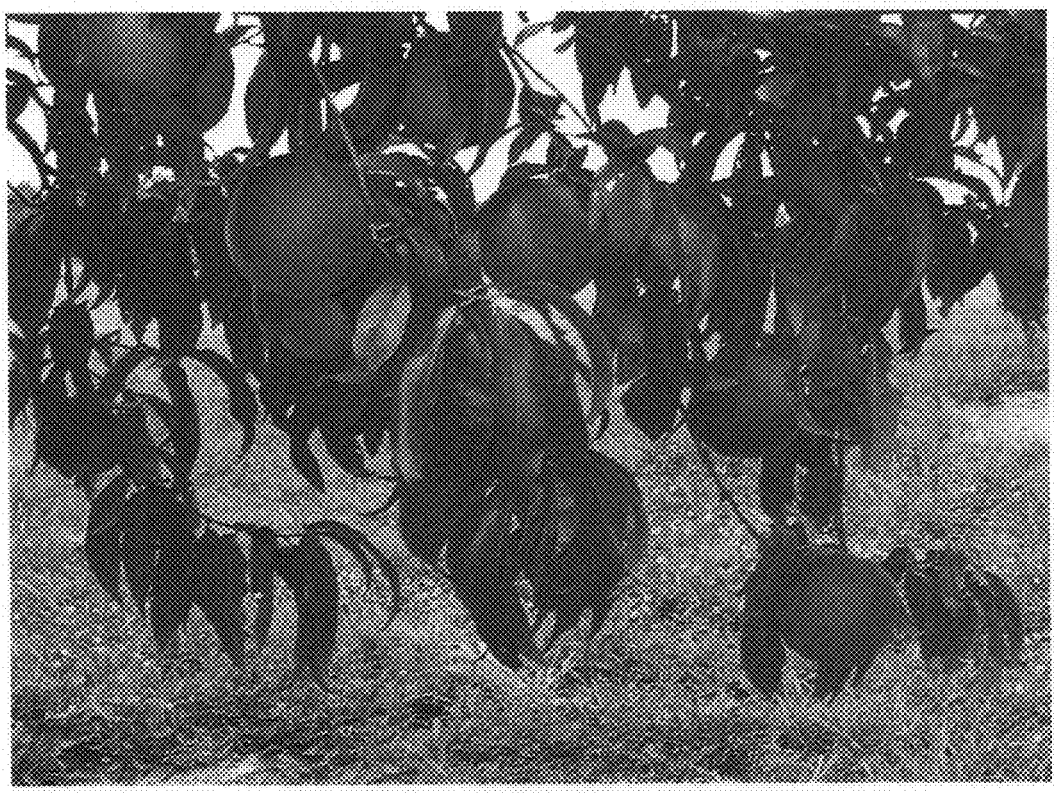

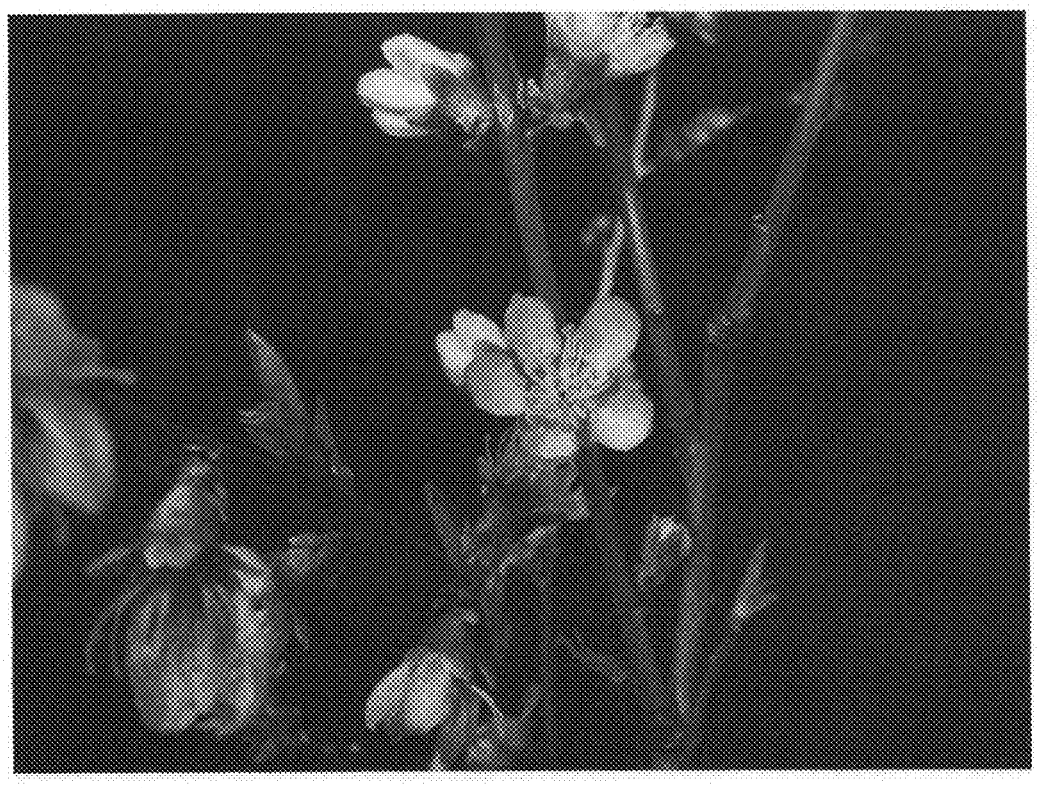

* * * * *